United States Patent
Op De Beek et al.

(10) Patent No.: US 6,931,093 B2
(45) Date of Patent: Aug. 16, 2005

(54) METHOD AND APPARATUS FOR VISUALIZING A 3D DATA SET

(75) Inventors: Johannes Catharina Antonius Op De Beek, Eindhoven (NL); Reiner Koppe, Hamburg (DE); Erhard Paul Artur Klotz, Nuemuenster (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 85 days.

(21) Appl. No.: 10/477,822

(22) PCT Filed: May 16, 2002

(86) PCT No.: PCT/IB02/01732

§ 371 (c)(1),
(2), (4) Date: Nov. 13, 2003

(87) PCT Pub. No.: WO02/093943

PCT Pub. Date: Nov. 21, 2002

(65) Prior Publication Data

US 2004/0131149 A1 Jul. 8, 2004

(30) Foreign Application Priority Data

May 16, 2001 (EP) .............................................. 01201843

(51) Int. Cl.$^7$ ............................................ G01N 23/083
(52) U.S. Cl. .............................. 378/22; 378/4; 378/901
(58) Field of Search ............................ 378/4, 8, 15, 19, 378/21, 22, 23, 901

(56) References Cited

U.S. PATENT DOCUMENTS

| | | | |
|---|---|---|---|
| 4,662,379 A | | 5/1987 | Macovski |
| 4,920,491 A | * | 4/1990 | Eberhard et al. ........... 382/131 |
| 5,872,828 A | | 2/1999 | Niklason et al. |
| 6,751,285 B2 | * | 6/2004 | Eberhard et al. ............. 378/37 |

FOREIGN PATENT DOCUMENTS

WO    WO 00/68863    11/2000

OTHER PUBLICATIONS

Grass, M., et al.; Three–Dimensional Reconstruction of High Contrast Objects Using C–Arm Image Intensifier Projection Data; Computerized Medical Imaging & Graphics; Pergamon Press; vol. 23, No. 6, 1999; pp. 311–321.

Stiel, G.M., et al.; Digital Flashing Tomosynthesis: A Promising Technique for Antiocardiographic Screening; IEEE, No. 2 1993, pp. 314–321.

Moret, J., et al.; 3D Rotational Angiography: Clinical Value in Endovascular Treatment; MedicaMundi, vol. 42, Issue 3, 1998, pp. 8–14.

Hastreiter, P. et al.; Intuitive and Interactive Manipulation of 3D Datasets by Integrating . . . ;IMMD 9; Lehrstuhl fur Graphische Datenverarbeitung.

IVoR: Interactive and Intuitive Volume Rendering of 3D–Medical Data with 3D–Texture Mapping Technique; www–kismet.iai.fzk.de.

* cited by examiner

Primary Examiner—David V Bruce

(57) ABSTRACT

For imaging a 3D data set the method of the invention comprises the following steps in succession: acquisition of images, reconstructing a 3D data set, followed by visualization, the reconstruction being started with a limited initial range of orientations around the direction of a local midprojection from a starting point so as to be visualized, the acquisition being continued during visualization and the reconstruction being updated in accordance with the additional acquisition obtained up to a final result. In particular, the selected part comprises a first visualization covering a range of from about 40° to 60°, with a midprojection at about from 20° to 30°.

10 Claims, 3 Drawing Sheets

METHOD AND APPARATUS FOR VISUALIZING A 3D DATA SET

BACKGROUND OF THE INVENTION

The invention relates to a method as disclosed in the preamble of claim 1.

Several different technologies for generating a digital 3D imaging data set in a broadly medical environment have been in use, such as 3D-CT, 3D-MRI, 3D-Ultrasound, 3D-Rotational Angio, 3D Rotational X-ray, and others. The medical environment includes without limitation the use of such visualizing for therapy planning, exploration, teaching, or veterinary, generally as applied to various tissue types that are relevant for living matter. Medica mundi, Vol. 42, No. 3, pp. 8–14, November 1998 describes a method for imaging a 3D volume of structures which comprises the following steps in succession: acquisition of images, collecting these images in a suitable manner for further processing, reconstructing a 3D image after previous correction, followed by visualization. The present inventors have recognized further advantages that may be attained by starting the reconstruction after acquisition with a limited initial range, followed by successive reconstructions of increasingly larger ranges until the full range has been obtained. In particular, such method would allow a view of the condition of the relevant area in an early stage of the acquisition in addition to the possibility of obtaining information from various angles of observation. The inventors have also recognized that in addition to customary visualization methods, the viewing of the above ranges would further allow the use of tomographic visualization to provide a user with even more pregnant information on the spatial details of the object under consideration.

SUMMARY OF THE INVENTION

Therefore, it is an object of the invention to visualize an initial image of a limited range from a starting point, followed by visualizing subsequent images of continuously broader ranges, until the full range has been obtained. Therefore, according to one of its aspects the invention is characterized as disclosed in the characterizing part of claim 1. Further advantageous aspects of the invention are recited in dependent claims.

BRIEF DESCRIPTION OF THE DRAWING

These and further aspects and advantages of the invention will be discussed more in detail hereinafter with reference to the disclosure of preferred embodiments, and in particular with reference to the appended Figures, in which.

GENERAL CONSIDERATIONS

Figure 1:
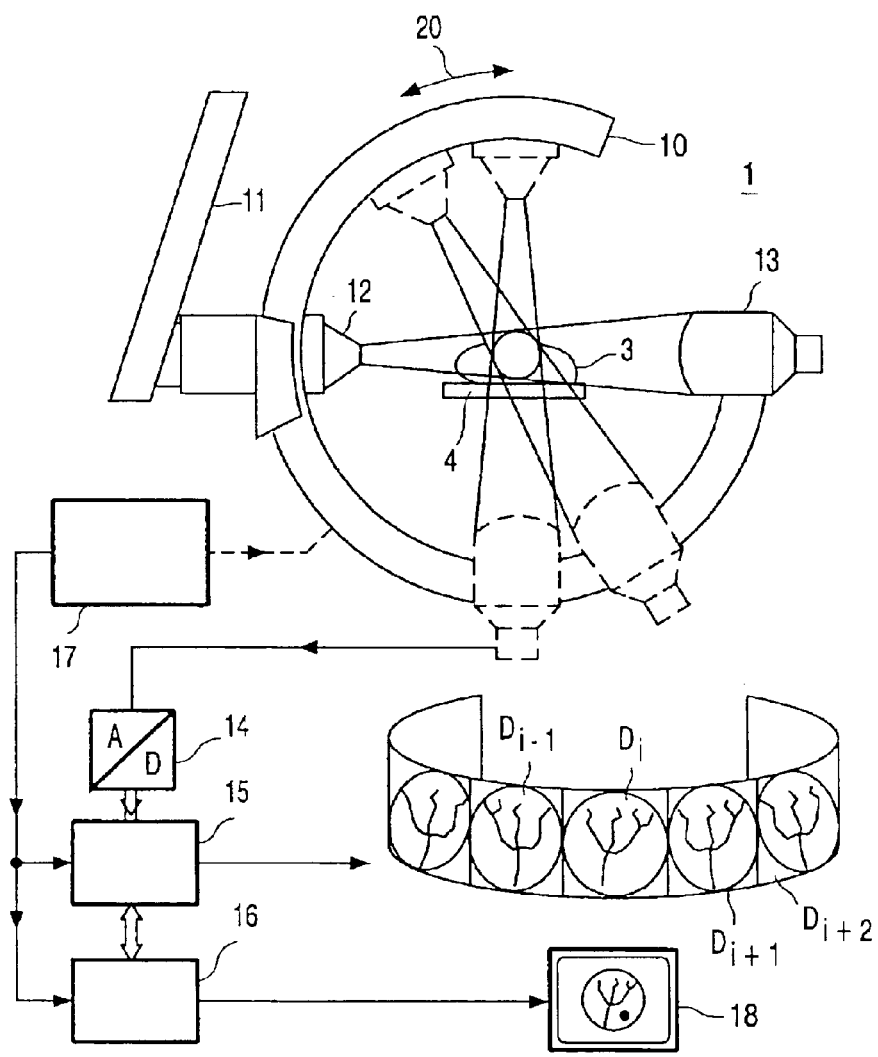
FIG. 1 shows an apparatus for acquiring images such as shown in the FIGS. 2a–e.

With respect to considering the method according to the present invention, the inventors have recognized the feasibility of tomosynthesis as an additional generating technology for the data set. By itself, the tomosynthesis technology focuses on getting only a single plane of image points sharp, but a subsequent parallel shifting or stepping of this plane will allow a region that has a similar character to be covered. Moreover, the rotating of such single plane over the stereoscopic angle in the same range of values as stated above will retain the original sharpness and resolution of the single image plane, so that through stepping the stereoscopic pair of planes the technology of tomosynthesis will also allow for applying the principles of the tomographic approach as described above.

An additional advantage obtained by the method according to the present invention is that the time required for obtaining the first visualization is substantially shorter than the time required for obtaining the visualization of the complete range.

DETAILED DESCRIPTION OF PREFERRED EMBODIMENTS

The procedure of the present invention will generally start by applying a conventional two-dimensional imaging method such as an X-ray scan to an intended object. 3D rotational X-ray data set is obtained by repeating the 2D operation along various axes, such as by rotating the object over 180° around an axis that is generally perpendicular to the axis of the "line-of-sight" of the X-rays. Decreasing the above rotation angle substantially below 180° will lower the eventual viewing quality. On the other hand, increasing the rotation angle substantially above 180° is generally not cost-effective when it should provide more information. The original paper in the field is L. A. Feldkamp et al, "Practical Cone-Beam algorithm", J. Opt. Soc. Am. A/Vol. 1, No. 6, June 1984, pages 612–619A. Reference is also made to a paper by M. Grass et al, "Three-Dimensional Reconstruction of High Contrast Objects Using C-Arm Image Intensifier Projection Data", Computerized Imaging and Graphics, Vol. 23 (1999), pages 311–321, inter alia to various resultant images. These algorithms or other high-powered computation algorithms will convert the data set into a 3D point-related data set. This 3D data set may immediately be used for rendering a 3D image of the object on a display screen. This image may be subjected to various motions, such as shifting or rotating, in order to obtain the best possible view of the object that may allow to distinguish between arteries, bone, organs and tissues of various other kinds as displayed.

The present inventors have recognized that a substantial improvement in image quality will be attainable by clipping off such information that would relate to unwanted or uninteresting points in space, thus allowing a major improvement in effective visualization conditions. For example, the viewing of tissue regions behind certain bone structures is greatly enhanced when the points associated with these bone structures are excluded from consideration by clipping. Similar considerations apply to structures behind the region of interest. The same considerations apply to other diagnostic technologies, such as 3D-MRI, 3D-Ultrasound, 3D-Rotational Angio, 3D-Rotational X-ray, and others.

By itself, the use of clipping has been posed by Huseyin Kemal, in "IVOR: Interactive and Intuitive Volume Rendering of 3D-Medical Data with 3D-Texturing Mapping Technique", htt://iregtl.iai.fzk.de/VRTRAIN/diplomarbeit.htm. Therein, three mutually perpendicular clipping planes are used, but it has been found that limiting the imaged region to an intermediate region between first and second clipping planes is much more useful in the present operating context than the cited Kemal technique.

FIG. 1 shows a device for carrying out the method according to the invention. The reference numeral 1 in FIG. 1 denotes an imaging device which serves to form two-dimensional X-ray images of an object 3 to be examined, for example a patient who is arranged on a table 4. The imaging device 1 includes an X-ray source 12 and an X-ray image pick-up device 13 which are aligned relative to one another and mounted on an arc of circle section 10 (a so-called C-arm) which itself is journalled in a stand 11 which is only partly shown. The C-arm 10 itself can be pivoted around a perpendicular axis on the one hand and be rotated around its center in the direction of the double arrow 20 on the other hand, for example through 180°, by means of a motor drive (not shown). During this motion a plurality of X-ray images can be formed which reproduce the examination zone 3,4 from different angular positions (some of which are denoted by dashed lines) of the image pick-up system 12,13. The X-ray image pick-up device 13 may be an X-ray image intensifier whereto a television chain is connected, the output signals thereof being digitized by an analog-to-digital converter 14 in order to be stored in a memory 15, so that at the end of the examination the entire series of X-ray images will have been stored. These X-ray images can be processed by an image processing unit 16. The images formed ( . . . $D_{-1}$, $D_i$, $D_{i+1}$, $D_{i+2}$ . . . ) can be displayed on a monitor 18 as a series of images over successively increasing ranges. The individual components of the X-ray device are controlled by means of a control unit 17, which comprises a unit governing display of the successively increasing ranges.

FIGS. 2a–2e illustrate the results obtained by visualizing the various ranges.

Figure 2A:
FIGS. 2a–2e show the gradual development of the spatial image at 0°–60° (midprojection 30°), 0°–90° (midprojection 45°), 0°–120° (midprojection 60°) and 0°–150° (midprojection 75°), respectively, to the full spatial image over the range of 0°–180° (mid-projection 90°).

FIG. 2a shows the visualization of a hand after a limited range of 60° (midprojection 30°) has been covered.

Figure 2B:

FIG. 2b shows the visualization of the hand after a limited range of 90° (midprojection 45°) has been covered.

Figure 2C:
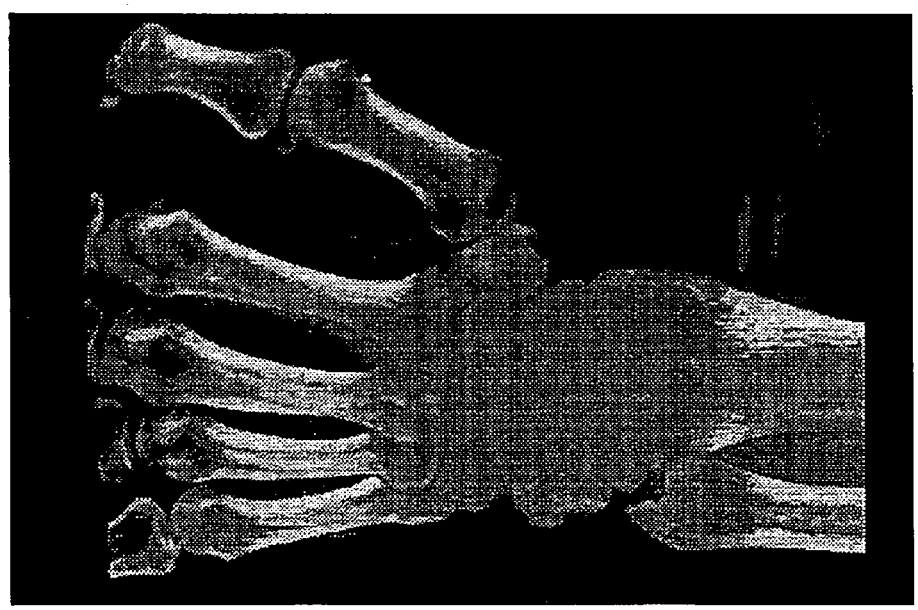

FIG. 2c shows the visualization of the hand after a limited range of 120° (midprojection 60°) has been covered.

Figure 2D:
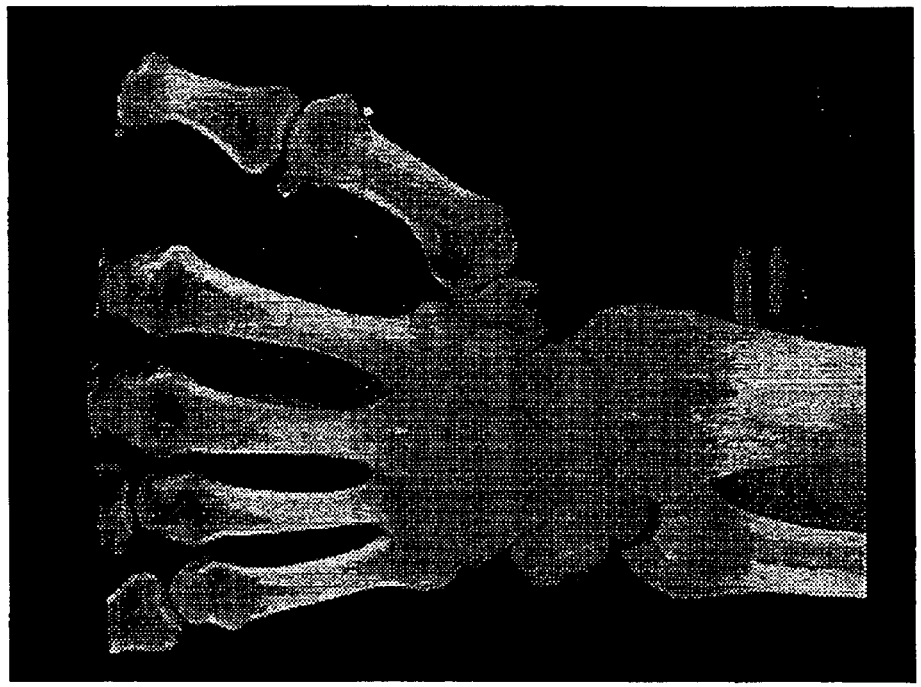

FIG. 2d shows the visualization of the hand after a limited range of 150° (midprojection 75°) has been covered.

Figure 2E:
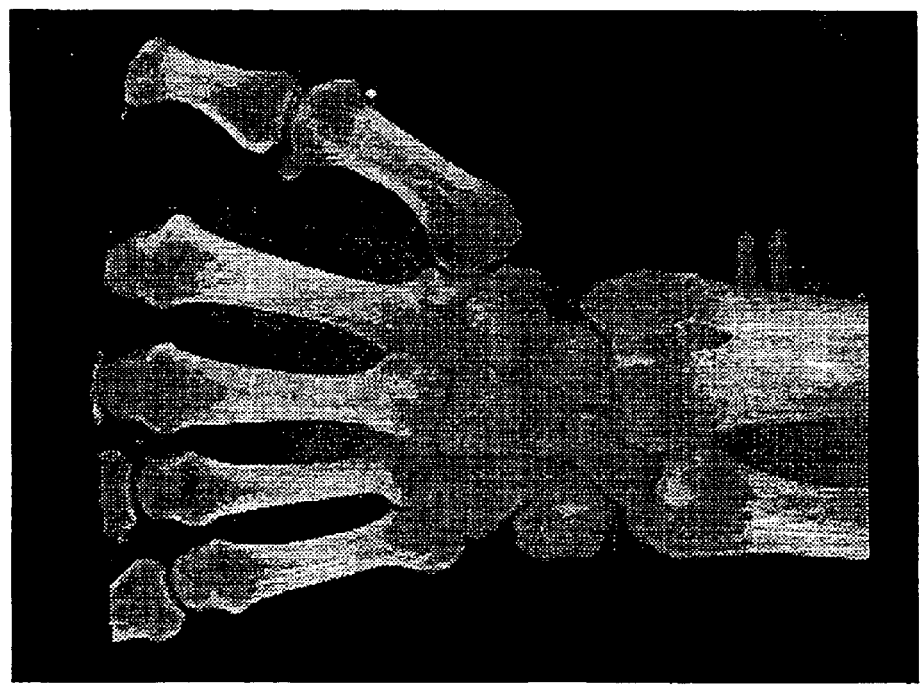

FIG. 2e shows the visualization of the hand after completion of the full range of about 180° along a midprojection of 90°.

In particular FIG. 2a offers early information on the object concerned in a limited period of time in comparison with the time required to obtain the full picture. In addition it allows a view of at least part of the "hidden part" of the hand as shown in FIG. 2e.

Figure 3:
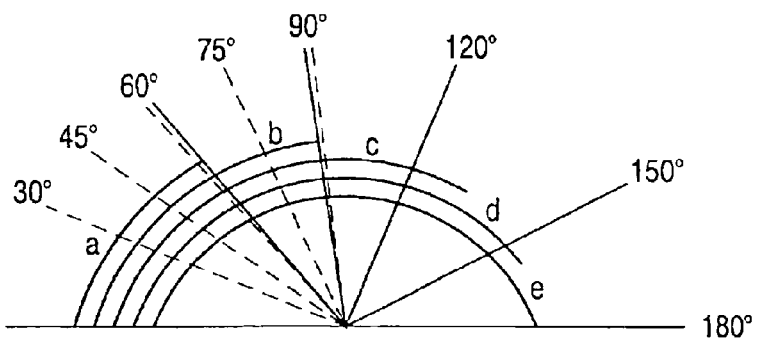
FIG. 3 shows a survey of the successive steps in developing a full spatial spectroscopic image with various ranges and their corresponding midprojection as shown in the FIGS. 2a–2e.

FIG. 3 is a survey of the various ranges over which the visualizations are obtained, together with their midprojections.

If applicable, a specific imaged structure thus found may be stored in memory for repetitive usage. By itself, persons of ordinary skill in the art of medical imaging will recognize the technology of tomosynthesis and reference is made in this respect to standard university textbooks.

What is claimed is:

1. A method for imaging a 3D data set, said method comprising the following steps in succession: acquisition of images, reconstructing a 3D data set, followed by visualization, said method being characterized in that initially the reconstruction is started with a limited initial range of orientations around the direction of a local midprojection from a starting point and is visualized, said acquisition being continued during visualization and the reconstruction being updated in accordance with the additional acquisition obtained up to a final result.

2. A method as claimed in claim 1, wherein said first reconstruction covers a range of from about 40° to 60° from the starting point, with a midprojection at about from 20° to 30°.

3. A method as claimed in claim 1, wherein said first reconstruction is followed by a second reconstruction covering a range from the starting point of about from 60° to 90°, with a midprojection at about from 30° to 45°.

4. A method as claimed in claim 1, wherein said reconstruction is continued until the full range has been covered.

5. A method as claimed in claim 1, wherein visualization is carried out immediately after completion of the reconstruction of a range.

6. A method as claimed in claim 1, wherein the final reconstruction covers a range of 180°.

7. A method as claimed in claim 1, wherein said first reconstruction covers a range of from about 40° to 60° from the starting point, with a midprojection at about from 20° to 30°.

8. A method as claimed in claim 1, wherein said first reconstruction is followed by a second reconstruction covering a range from the starting point of from about 60° to 90°, with a midprojection at from about 30° to 45°.

9. An apparatus for visualizing continuously increasing ranges of a 3D medical data set, said apparatus comprising:
an X-ray source (12) which may be moved with respect to an object (3) to be investigated and faces at least one X-ray detector (13) for collecting the images over a range with data processing means (16), said apparatus being characterized in that it comprises means allowing visualization of at least one set of X-ray images over a range of less than 180° with the X-ray image in a plane perpendicular to the midprojection of the range, and continued extension of the range.

10. An apparatus as claimed in claim 9, wherein the final range covers 180°.

* * * * *